United States Patent

Browne et al.

[11] Patent Number: 6,099,305
[45] Date of Patent: Aug. 8, 2000

[54] DEVICE FOR THE PRODUCTION OF A DENTAL WORKING MODEL FOR PREPARATION OF A PROSTHETIC WORK

[75] Inventors: Lawrence Stephen Browne, Worplesdon; Raymond Terence Clenton, Bognor Regis; Trevor Howard Neve, Arundel; Derren Neve, Worthing, all of United Kingdom

[73] Assignee: Regency Technologies Limited, Bognor Regis, United Kingdom

[21] Appl. No.: 09/202,055

[22] PCT Filed: Jun. 4, 1997

[86] PCT No.: PCT/GB97/01508

§ 371 Date: Dec. 3, 1998

§ 102(e) Date: Dec. 3, 1998

[87] PCT Pub. No.: WO97/46171

PCT Pub. Date: Dec. 11, 1997

[30] Foreign Application Priority Data

Jun. 4, 1996 [GB] United Kingdom .................. 9611600
Nov. 28, 1996 [GB] United Kingdom .................. 9624814

[51] Int. Cl.[7] .............................. A61C 19/00; A61C 9/00
[52] U.S. Cl. ................................ 433/34; 433/47; 433/60
[58] Field of Search .................................. 433/34, 35, 36, 433/48, 60, 74, 47

[56] References Cited

U.S. PATENT DOCUMENTS

| | | |
|---|---|---|
| 4,059,902 | 11/1977 | Shiokawa . |
| 4,116,416 | 9/1978 | Segura . |
| 4,283,173 | 8/1981 | Browne et al. ........................ 433/34 |
| 4,494,934 | 1/1985 | Huffman . |
| 4,708,648 | 11/1987 | Weissman .............................. 433/34 |
| 4,842,505 | 6/1989 | Zeiser ..................................... 433/34 |
| 4,957,435 | 9/1990 | Jinoian et al. . |
| 5,129,822 | 7/1992 | Dobbs .................................... 433/34 |
| 5,297,960 | 3/1994 | Burns . |
| 5,328,366 | 7/1994 | Callne . |
| 5,506,095 | 4/1996 | Callne .................................... 433/34 |

FOREIGN PATENT DOCUMENTS

| | | |
|---|---|---|
| 4306147 | 9/1994 | Germany . |
| 2023429 | 1/1980 | United Kingdom . |

*Primary Examiner*—Nicholas D. Lucchesi
*Attorney, Agent, or Firm*—Kinney & Lange, P.A.

[57] ABSTRACT

A device for the production of a dental working model for preparation of a prosthetic work comprises a body member having a blind arcuated cavity bounded by facing inner and outer cavity walls, for receiving semi-liquid model material. The blind end of the arcuate cavity is closed by a sacrificial membrane which is integral with the body member. The membrane is of sufficient thickness to contain the semi-liquid model material within the arcuate cavity and of sufficient thinness to be easily removed, for example, by grinding.

21 Claims, 2 Drawing Sheets

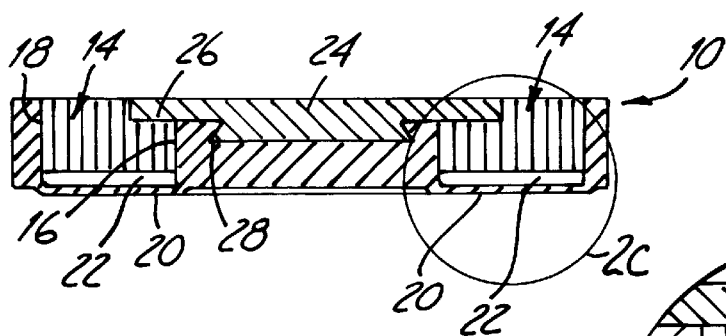
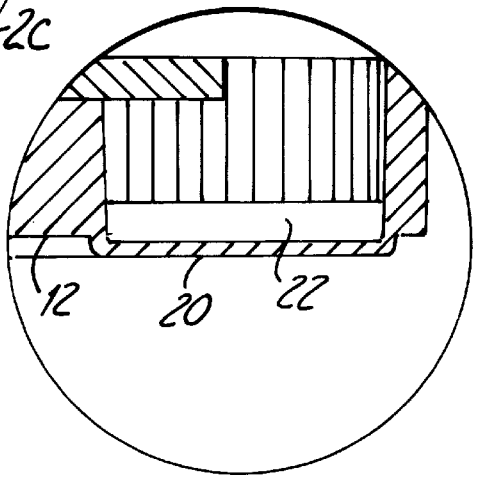
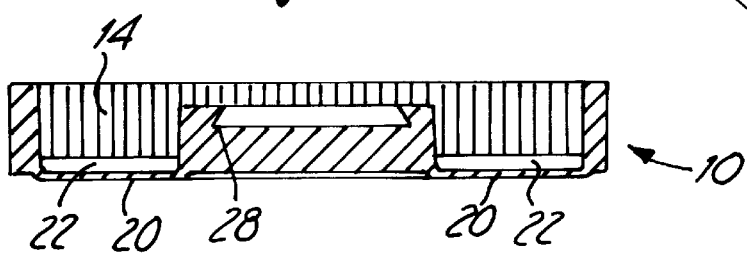
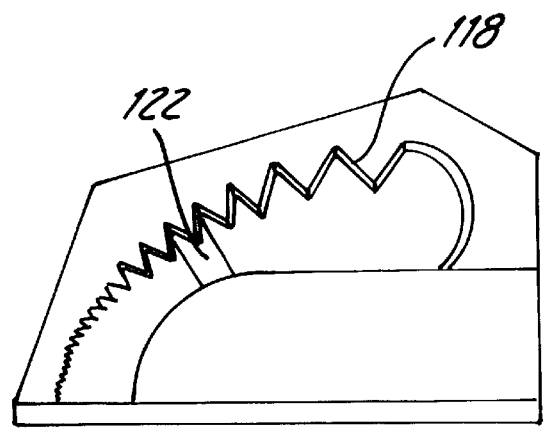

DEVICE FOR THE PRODUCTION OF A DENTAL WORKING MODEL FOR PREPARATION OF A PROSTHETIC WORK

The present invention relates to a device for the production of a dental working model for preparation of a prosthetic work and to a method of producing a dental working model using such a device.

The production of dental prostheses requires the production of a dental working model which is an exact duplication of the patient's mouth on which a prosthesis can be fabricated. Typically, a dental working model comprises a positive model of the teeth, as well as possibly the gum, mandible portions, palate etc., of one jaw of the patient fixed onto a substrate. The particular teeth of the model on which a dental prosthesis is to be produced can then be sectioned from the whole model (to produce what is termed a "die"). During preparation of the prosthesis, it is necessary to be able to relocate the individual dies into their original positions on the model to ensure that the prosthesis will fit the patient.

Errors in the final product can be caused by any system where the dies appear to have been properly relocated but, in fact, are a minute amount out from their correct position. When the prosthesis is completed, it will fit this working model containing the teeth on which the prosthesis is to be located and will occlude with the opposing model (of the teeth on the other jaw) but will not necessarily fit the patient's mouth. It is then necessary for the prosthesis to be trimmed to obtain a proper fit or indeed for the prosthesis to be totally remade, wasting time and money.

Dental working models are produced typically in dental die stone or other model material which is semi-liquid when cast but hard when cured. First of all, impressions of the two jaws of the patient's mouth are taken, typically in a silicone impression material. This impression is filled with the semi-liquid model material to produce a positive model of the patient's mouth. In addition, some form of tray or model former is also filled with the semi-liquid model material to produce the substrate. A filled impression of one jaw of the patient's mouth is inverted onto the substrate. When the model material has cured, an integral model of the jaw of the patient is produced which can then be sectioned as outlined above.

There has long been a need for dental technicians to have an accurate registration device that will enable them to section dental models into individual dies then reinstate the sections of the model to their former relationship with the adjacent dies and also the opposing model. This correct relationship is crucial to the manufacturing process of the prosthesis.

U.S. Pat. No. 4,283,173 (Browne et al) discloses a device for the production of a dental working model for the preparation of prosthetic works comprising a base presenting an open portion on both sides. A hollow portion adapted to the shape of the jaws presents ribs on both inner surfaces. The ribs act as retaining members for the model material and have the shape of ramps with a constant slope from top to bottom, the hollow portion widening from bottom to top. Because the base presents an open portion on both sides, the relocation of the dies can be checked from both the top and the bottom. However, an open bottom tray cannot contain the soft semi-liquid model material. As the semi-liquid model material is poured into the open bottom tray positioned on a bench surface (or other surface), the semi-liquid model material tends to creep through the gap between the tray and the bench surface causing a flash to appear on the model. This flash cannot be cleaned off the model effectively and causes inaccuracies in the relocation process.

Other devices using a separate bottom cover plate which fixes to the lower edge of the tray have been partially successful in containing the semi-liquid model material. However, there is still a tendency for the semi-liquid to creep through the seal between the separate bottom cover plate and the lower edge of the tray causing a flash to appear on the model. is Because of these problems, the technician must be extremely fastidious when pouring the model material into the tray and subsequent operations, making current systems technique-sensitive.

It is an object of the present invention to provide an improved device for the production of a dental working model for preparation of a prosthetic work.

According to a first aspect of the present invention there is provided a device for the production of a dental working model for preparation of a prosthetic work comprising:

a body member having a blind arcuate cavity bounded by facing inner and outer cavity walls, for receiving semi-liquid model material, the blind end of the arcuate cavity being closed by a membrane, the membrane being integral with the body member and being of sufficient thickness to contain the semi-liquid model material within the arcuate cavity and being of sufficient thinness to be easily removed.

The provision of such a sacrificial membrane to define a blind arcuate cavity in which the semi-liquid model material is poured eliminates the risk of a flash appearing on the dental working model due to leakage of semi-liquid model material at the base of the working model and thereby reduces the risk of inaccuracies in the relocation process. After the die material has cured, the sacrificial membrane is removed, e.g. by grinding, to reveal the underside of the working model and so allow a technician to ascertain when dies have been relocated fully and exactly in the body member. This sacrificial membrane eliminates the need for other aids to the vertical relocation of the dies and so enables the device to be manufactured more economically and so be unique to each model.

Advantageously, the external surface of the sacrificial membrane projects externally of the external surface of the body member from which the membrane is formed. This feature reduces the amount of material to be ground away for the same thickness of membrane. The internal surface of the membrane may be coplanar with the external surface of the body member from which the membrane is formed. Advantageously, the arcuate cavity projects beyond the external surface of the body member from which the membrane is formed. This feature enables the operator to be able to discern, during grinding, when sufficient of the membrane has been removed to expose the die material to view.

To reduce the amount of material to be removed during grinding, the sacrificial membrane has the same shape in plan view as the arcuate cavity.

The sacrificial membrane is formed as one piece with the body member to eliminate any risk of semi-liquid model material leaking through.

Typically, the sacrificial membrane has a thickness in the range of from 0.2 to 0.9 mm. This range of thicknesses provides a membrane which is sufficiently strong and rigid to contain the semi-liquid model material but sufficiently thin to be easily and quickly removed typically by the grinding process.

Typically, the device is made of a plastics material.

According to a second aspect of the present invention there is provided a device for the production of a dental working model for preparation of a prosthetic work comprising a body member having an arcuate cavity bounded by facing inner and outer cavity walls and releasable projection means for projecting across said inner cavity wall into the arcuate cavity.

The provision of releasable projection means for projecting across said inner cavity wall into the arcuate cavity allows the dental working model to be retained in the device even after the dental working model has been cut into the individual dies. When the semi-liquid model material is poured into the arcuate cavity, the releasable projection means is projecting into the arcuate cavity and so forms a groove in the model material which is present in the finished dental working model. The releasable projection means is released to enable the working model to be removed from the device and sectioned. When the dies are relocated in the arcuate cavity, the releasable projection means projects into the groove in the dies of the dental working model, enabling the dies to be retained in the device during subsequent working and transit.

For simplicity, the releasable projection means has a first position extending across the top of said inner cavity wall. Advantageously, said releasable projection means comprises a plate.

To assist relocation of the dies, each of said cavity walls has a plurality of projections extending into the arcuate cavity. Advantageously, the pitch and/or amplitude of the projections on each of said cavity walls varies with separation from one end of each of said cavity walls. Most preferably, said plurality of projections comprises a plurality of serrations.

Accordingly, a third aspect of the present invention provides a device for the production of a dental working model for preparation of a prosthetic work comprising:

a body member having an arcuate cavity bounded by facing inner and outer cavity walls, at least one of said cavity walls having a plurality of projections extending into the arcuate cavity wherein the pitch of the projections varies with separation from one end of said cavity wall, the pitch between any pair of adjacent projections being different from the pitch between at least one adjacent pair of adjacent projections.

Furthermore, a fourth aspect of the present invention provides a device for the production of a dental working model for preparation of a prosthetic work comprising:

a body member having an arcuate cavity bounded by facing inner and outer cavity walls, at least one of said cavity walls having a plurality of projections extending into the arcuate cavity wherein the amplitude of the projections varies with separation from one end of said cavity, the amplitude of each projection being different from the amplitude of at least one adjacent projection.

Embodiments of the present invention will now be described, by way of example only, and with reference to the accompanying drawings in which:

FIG. 2a shows a cross-section of the embodiment of FIG. 1 along the line II—II with the retaining plate in place;

FIG. 2b shows a cross-section of the embodiment of FIG. 1 along the line II—II with the retaining plate removed;

FIG. 2c shows part of FIG. 2a in greater detail;

FIG. 2d shows schematically part of the cavity wall of FIG. 1 in greater detail.

Figure 1:
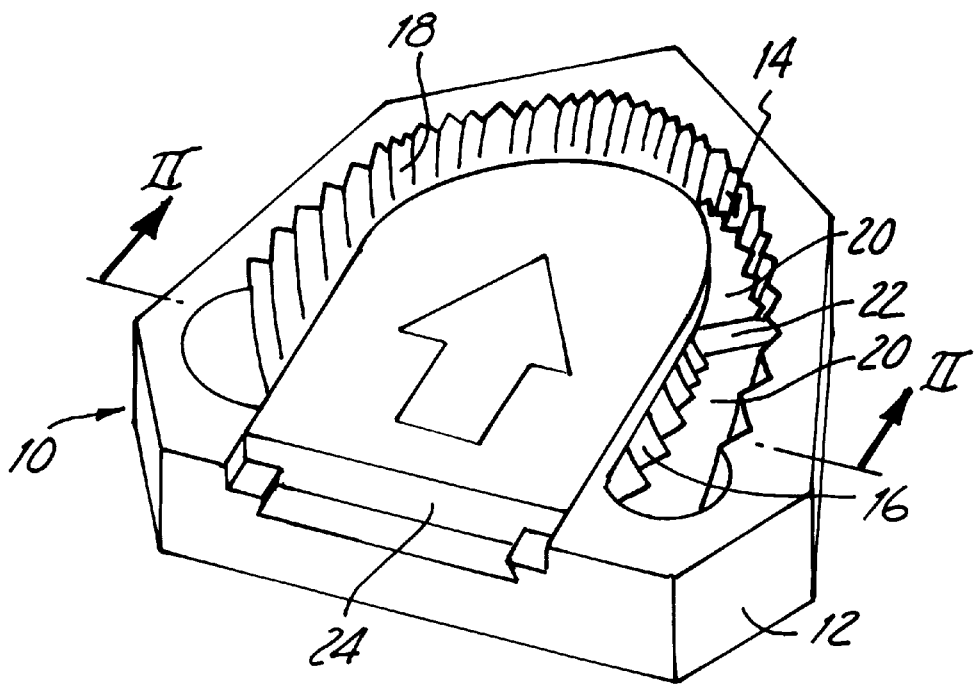
FIG. 1 shows a perspective view of a first embodiment of the invention including a retaining plate.

FIG. 1 shows a dental tray provided in accordance with an embodiment of the present invention for receiving the semi-liquid model material to produce the substrate for a dental working model. As outlined above, the dental tray member also assists in relocation of the sectioned dies of the dental working model after the dental working model has been sectioned. The dental tray comprises a body member 12 having a blind arcuate cavity 14 bounded by an inner arcuate cavity wall 16 and an outer arcuate cavity wall 18. The base of the body member 12—and hence the blind end of the blind arcuate cavity 14—is closed by a sacrificial membrane 20 typically having a thickness in the range of 0.2 mm to 0.9 mm. To increase the rigidity of the dental tray 10, the inner and outer cavity walls 16, 18 are also joined by a plurality of support webs 22 (one of which can be seen in FIG. 1 and two of which can be seen in FIGS. 2a and 2b). Each of the inner and outer cavity walls 16, 18 has a plurality of serrations projecting into the cavity 14. The cavity walls are symmetrical about a plane through the midpoint of the cavity walls and transverse to the plane of the base member. The pitch and amplitude of the serrations varies such that adjacent projections in each half of the cavity wall have a different pitch and amplitude and thus prevents transposition of individual dies in the dental tray.

As shown also in FIG. 2a, the dental tray also incorporates a releasable retaining plate or tongue 24 in the dovetail 28 which can be removed as shown in FIG. 2b. (As an alternative to the dovetail 28, a slot can be used.) The releasable retaining plate has a lip 26 which projects across the inner cavity wall 16 into the arcuate cavity 14.

To produce a dental working model, semi-liquid model material is poured into the blind arcuate cavity 14 of the dental tray 10 with the retaining plate 24 in the position shown in FIGS. 1 and 2a. An impression of one jaw of the patient's mouth is also filled with semi-liquid model material and the filled impression is inverted onto the dental tray 10. When the model material has cured, the impression is removed to reveal a positive model reproducing one jaw of the patient's mouth. The models of the upper and lower jaws of the patient's mouth are then placed into direct opposition with each other and, by use of a device called an articulator known to those skilled in the art, the correct correlationship of the patient's jaws are transferred to the models. After this stage, the models are removed from the articulator. The sacrificial membrane 20 is removed from the dental tray 10 containing the working model. The sacrificial membrane 20 acts as a separator during articulation. The sacrificial membrane and the model material are trimmed at the same time, ensuring that the underside of the tray and the working model are now in a perfect plane and that any elastic memory, shrinkage or expansion of the die material during curing will thus be compensated for during the removal of the sacrificial membrane. At this point, the dental working model is removed from the tray and then can be replaced so that any deficiency in location can be easily detected at the interface generated during removal of the sacrificial membrane.

As can be seen most clearly in FIG. 2c, the external surface of the sacrificial membrane 20 is not coplanar with the external surface of the body member 12 but, rather, projects externally of the external surface of the body member 12. The internal surface of the sacrificial membrane 20 may, in some embodiments, be coplanar with the external surface of the body member 12. Preferably, as shown in FIG. 2c, the arcuate cavity 14 extends beyond the external surface of the body member 12 itself. Thus, when the sacrificial membrane and the model material are being removed, the operator will be able to hear a difference in the sound of the grinding as all of the sacrificial membrane 20 is removed and the underside of the working model is being ground.

The cured dental working model is sectioned into the individual dies which can be removed from the tray to be worked on. In order to ensure absolute accuracy of relocation of the separated dies, the following procedure is the recommended method for sawing and separating the individual dies from the overall cast model. Following removal of the sacrificial membrane 20, and any excess model material around the face of the tray, the complete model is reseated into the tray and the newly exposed model interface checked for accuracy of position. The newly exposed model base should be clearly aligned with the tray bottom and the periphery of the tray sides should also be in intimate contact with the model. This can be checked by reinserting the plate 24 fully. With a sharpened pencil, the model is marked with a line all around the tray sides at the point where the model emerges from the tray. A second line is marked parallel to the first but at least 2 mm further from the tray rim. A fine bladed piercing saw is used to cut down to the top line on each side of the required die. When all of the separating cuts have been made to this line, the model is carefully removed from the surrounding tray and sawn from the base of the model up to the bottom line. This will leave the dies connected by the uncut 2 mm, +/−, isthmus of model material. The remaining connecting die material can then be snapped. This fractured portion will only marry exactly to its counterpart thus ensuring an absolute location and relocation of the individual dies and sections. The model tray is so designed to allow positive and accurate relocation to the satisfaction of the individual technician. The above procedure is offered as the recommended method of maximising the accuracy of the device but is not an absolute requirement.

As already outlined above, the inner and outer cavity walls 16, 18 have serrations of an infinitely variable pitch and/or amplitude (shown schematically in FIG. 2d) such that each die will fit only into the part of the tray from which it came. As the sacrificial membrane 20 has been removed, the underside of the tray can be checked to ascertain that any die has been properly relocated in the tray. The final step of the method used to separate the dies involves snapping a retaining portion linking each die. This leaves a small irregular section on each die which can only be remated with the corresponding small irregular section of the adjacent die. Thus, the serrations of infinitely variable pitch and amplitude, the option of being able to visually check the interface at the underside of the tray and model and the irregular nature of the snapped retaining part edges provide a three point check that accurate relocation of the dies has been obtained.

To enable the dental working model to be removed from the tray 10, the retaining plate 24 is removed by being slid from the dovetail 28. Projection of the lip 26 of the plate 24 into the arcuate cavity 14 results in a corresponding groove in the dental working model. When the sectioned dies are relocated in the tray 10, the retaining plate 24 can be replaced to lock into the groove in the dies and so confirm and hold the individual dies in their exact position within the tray 10. The cavity 14 is wider at the top than at the base so that the slope of the cavity walls 16, 18 assists in holding the working model when the sacrificial membrane has been removed.

Figure 3:
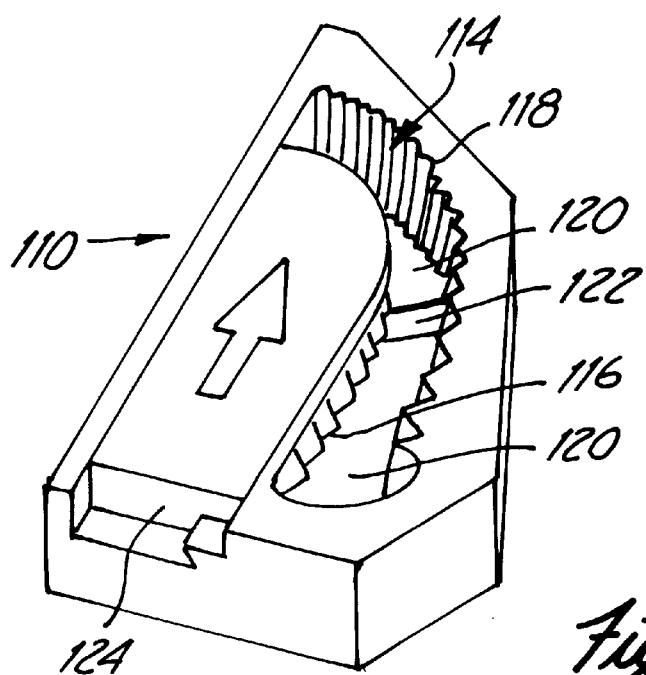
FIG. 3 shows a perspective view of a second embodiment of the present invention.

FIG. 3 shows a tray 100 suitable for production of a quadrant dental working model, i.e. a model of one half of the arch of the jaw. Reference numerals starting in the "100 series" but otherwise corresponding to the reference numerals of FIGS. 1, 2a and 2b are used to designate similar features in the embodiments of FIGS. 1 and 3.

What is claimed is:

1. A device for the production of a dental working model for preparation of a prosthetic work comprising:

a body member having a blind arcuate cavity bounded by facing inner and outer cavity walls, for receiving semi-liquid model material, the blind end of the arcuate cavity being closed by a sacrificial membrane, the sacrificial membrane being integral with the body member and being of sufficient thickness to contain the semi-liquid model material within the arcuate cavity and being of sufficient thinness to be easily removed.

2. A device according to claim 1 wherein the external surface of the sacrificial membrane projects externally of the external surface of the body member from which the sacrificial membrane is formed.

3. A device according to claim 2 wherein the internal surface of the sacrificial membrane is coplanar with the external surface of the body member from which the sacrificial membrane is formed.

4. A device according to claim 2 wherein the arcuate cavity projects beyond the external surface of the body member from which the sacrificial membrane is formed.

5. A device according to claim 1 wherein the sacrificial membrane has the same shape in plan view as the arcuate cavity.

6. A device according to claim 1 wherein the sacrificial membrane is formed as one piece with the body member.

7. A device according to claim 1 wherein the sacrificial membrane has a thickness in the range of 0.2 to 0.9 mm.

8. A device according to claim 1 formed of a plastics material.

9. A device according to claim 1 wherein at least one of said cavity walls has a plurality of projections extending into the arcuate cavity.

10. A device according to claim 9 wherein the pitch of the projections varies with separation from one end of said cavity wall.

11. A device according to claim 10 wherein the pitch between any pair of adjacent projections is different from the pitch between at least one adjacent pair of adjacent projections.

12. A device according to claim 10 wherein the amplitude of the projections on each of said cavity walls varies with separation from one end of each of said cavity walls.

13. A device according to claim 12 wherein the amplitude of each projection is different from the amplitude of at least one adjacent projection.

14. A device according to claim 9 wherein said cavity walls are symmetrical about a plane extending through the midpoint of the cavity walls and transverse to the plane of the base member.

15. A device according to claim 9 wherein said plurality of projections comprises a plurality of serrations.

16. A device according to claim 1 further comprising releasable projection means for projecting across said inner cavity wall into the arcuate cavity.

17. A device according to claim 16 wherein said releasable projection means has a first position extending across the top of said inner cavity wall.

18. A device according to claim 16 wherein said releasable projection means comprises a plate.

19. A method of producing a dental working model for the preparation of a prosthetic work using the device of claim 1 comprising the steps of:

filling the arcuate cavity with semi-liquid model material; and removing the sacrificial membrane to reveal the underside of the cured model material in the arcuate cavity.

20. A method according to claim 19 wherein the sacrificial membrane is removed by grinding.

21. A device for the production of a dental working model for preparation of a prosthetic work comprising:

a body member having a blind arcuate cavity bounded by facing inner and outer cavity walls, the blind end of the arcuate cavity being closed by a sacrificial membrane integral with the body member.

* * * * *